(12) United States Patent
Lee et al.

(10) Patent No.: US 11,741,523 B2
(45) Date of Patent: Aug. 29, 2023

(54) PERSONALIZED SKINCARE RECOMMENDATIONS BASED ON BIOMARKER ANALYSIS

(71) Applicant: L'Oreal, Paris (FR)

(72) Inventors: Ji Lee, New York, NY (US); Guive Balooch, New York, NY (US); Aude Foucher, Aulnay-sous-Bois (FR); Nukhet Cavusoglu, Paris (FR)

(73) Assignee: L'Oreal, Paris (FR)

( * ) Notice: Subject to any disclaimer, the term of this patent is extended or adjusted under 35 U.S.C. 154(b) by 896 days.

(21) Appl. No.: 16/528,380

(22) Filed: Jul. 31, 2019

(65) Prior Publication Data
US 2021/0035185 A1 Feb. 4, 2021

(51) Int. Cl.
*G06Q 30/06* (2023.01)
*G06Q 30/0601* (2023.01)
*G06F 3/14* (2006.01)
*G01N 33/68* (2006.01)
*G01N 21/64* (2006.01)

(52) U.S. Cl.
CPC ..... *G06Q 30/0631* (2013.01); *G01N 21/6428* (2013.01); *G01N 33/6881* (2013.01); *G06F 3/14* (2013.01); *G01N 2021/6439* (2013.01)

(58) Field of Classification Search
CPC .......... G06Q 30/0631; G01N 21/6428; G01N 33/6881; G01N 2021/6439; G06F 3/14
See application file for complete search history.

(56) References Cited

U.S. PATENT DOCUMENTS

| 10,025,280 | B1 | 7/2018 | Bly | |
|---|---|---|---|---|
| 2005/0053637 | A1* | 3/2005 | Ma'Or | A61K 31/535 514/20.3 |
| 2008/0131902 | A1 | 6/2008 | Maor et al. | |
| 2009/0253162 | A1* | 10/2009 | Windsor | G01N 33/52 435/29 |
| 2012/0184448 | A1 | 7/2012 | Stella et al. | |
| 2016/0016171 | A1* | 1/2016 | Goel | B01L 3/5023 435/7.1 |
| 2016/0184566 | A1 | 6/2016 | Ibrahim et al. | |

(Continued)

FOREIGN PATENT DOCUMENTS

| JP | 2014041043 A | 3/2014 |
|---|---|---|
| KR | 20130135887 A | 12/2013 |

(Continued)

OTHER PUBLICATIONS

Office Action dated Feb. 25, 2022, issued in related U.S. Appl. No. 16/528,196, filed Jul. 31, 2019, 15 pages.

(Continued)

*Primary Examiner* — Tom Y Lu
(74) *Attorney, Agent, or Firm* — Christensen O'Connor Johnson Kindness PLLC

(57) ABSTRACT

In some embodiments, protein biomarker concentration information for a subject is obtained, and is used to determine one or more skin trends likely to be experienced by the subject. Skincare product recommendations are generated based on the protein biomarker concentration information. Feedback on the recommended skincare products may be received, and may be used to improve future recommendations for skincare products for the subject or for other subjects.

18 Claims, 4 Drawing Sheets

(56) References Cited

U.S. PATENT DOCUMENTS

| | | |
|---|---|---|
| 2017/0340267 A1 | 11/2017 | Shen et al. |
| 2018/0284729 A1 | 10/2018 | Orsita et al. |
| 2018/0328945 A1 | 11/2018 | Nova et al. |
| 2019/0237194 A1 | 8/2019 | Salvi et al. |
| 2019/0292577 A1 | 9/2019 | Amini et al. |
| 2019/0295728 A1 | 9/2019 | Jeong et al. |
| 2019/0303991 A1 | 10/2019 | Ford |
| 2019/0369119 A1 | 12/2019 | Zhuang et al. |
| 2020/0102600 A1 | 4/2020 | Amini et al. |
| 2020/0250866 A1 | 8/2020 | Balooch et al. |

FOREIGN PATENT DOCUMENTS

| | | |
|---|---|---|
| WO | 2018/109078 A1 | 6/2018 |
| WO | 2018/115517 A1 | 6/2018 |
| WO | 2018/187151 A1 | 10/2018 |
| WO | 2019/038290 A1 | 2/2019 |
| WO | 2019/239120 A1 | 12/2019 |

OTHER PUBLICATIONS

International Search Report and Written Opinion dated Jul. 30, 2021, issued in corresponding International Application No. PCT/US2020/042012, filed Jul. 14, 2020, 14 pages.

"Presentation of Team PeauUnique at L'Oreal Brandstorm 2019," May 23, 2019, 10 pages.

L'Oréal Brandstorm 2019—International Final Ceremony, YouTube clip, May 23, 2019, https://www.youtube.com/watch?v=CcLzr_4NhMA, Transcript 29 pages, see pp. 7-10 (timestamp 25:15 to timestamp 36:27).

Office Action dated May 23, 2023, in corresponding Japanese application No. 2022-506506, filed Nov. 4, 2019, 8 pages.

* cited by examiner

PERSONALIZED SKINCARE RECOMMENDATIONS BASED ON BIOMARKER ANALYSIS

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a computer-implemented method of providing a skincare product recommendation for a subject is provided. A computing device obtains protein biomarker concentration information. The computing device determines at least one skin trend based on the protein biomarker concentration information. The computing device determines at least one skincare product associated with the at least one skin trend. The computing device presents a recommendation of the at least one skincare product via a display.

In some embodiments, a system for providing a skincare product recommendation for a subject is provided. The system comprises circuitry for obtaining protein biomarker concentration information; circuitry for determining at least one skin trend based on the protein biomarker concentration information; circuitry for determining at least one skincare product associated with the at least one skin trend; and circuitry for presenting a recommendation of the at least one skincare product via a display.

In some embodiments, a computing device is provided that is configured to provide a skincare product recommendation for a subject, by obtaining protein biomarker concentration information; determining at least one skin trend based on the protein biomarker concentration information; determining at least one skincare product associated with the at least one skin trend; and presenting a recommendation of the at least one skincare product via a display.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

The medical field is currently being improved by the growing availability of biomarker analysis systems. These systems, which can operate in an outpatient or clinical setting, can provide a noninvasive measurement of various protein concentrations. These protein concentrations may then be used for various treatment-related purposes. Through clinical studies, certain proteins that can be detected by these biomarker analysis systems have been identified to be linked to clinical signs of aging, as well as responsiveness/non-responsiveness to various active ingredients of skincare products. For example, biomarkers such as YKL40, TG3, LCN1, IDE, and FLG2 have been found to be correlated with clinical signs of aging and responsiveness such as shiny skin, rough skin, uneven skin tone, eye wrinkles, photo aging, loss of elasticity, dilated pores, responsiveness to retinol, and responsiveness to proxylane.

Even though these correlations have been determined, the biomarker analysis system only provides raw protein concentration information, and does not use these correlations. What is desired are systems and methods that use the biomarker concentration information to generate skincare product recommendations and to improve such recommendations to address predicted skin trends.

Figure 1:
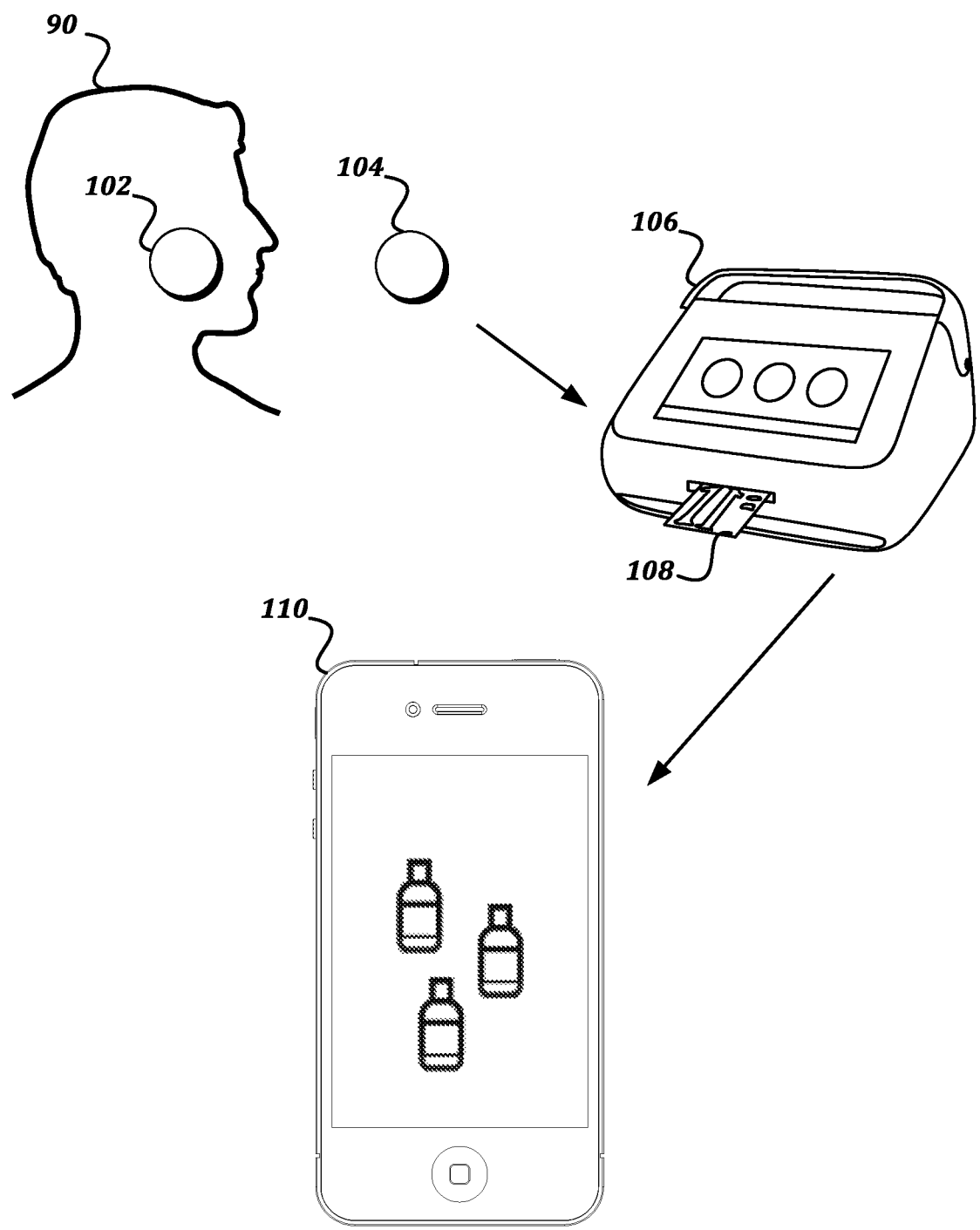
FIG. 1 is a high-level schematic drawing that illustrates various components of an example embodiment of a system according to various aspects of the present disclosure.

FIG. 1 is a high-level schematic drawing that illustrates various components of an example embodiment of a system according to various aspects of the present disclosure. The system is used to obtain a sample from a user 90, to generate skincare product recommendations based on the sample, and to improve the recommendations over time. As shown, one or more sampling disks 102, 104 are used to obtain a sample from the user 90. A sampling disk 104 is then processed by a protein extraction device 208, and a collected sample is applied to a test cartridge 108. The test cartridge 108 is inserted into an immunoassay analyzer device 106. The immunoassay analyzer device 106 determines concentrations of various protein biomarkers that are associated with various skin trends. The protein biomarker concentration information is then provided to a product recommendation computing device 110 to determine skin trends that are present. Based on the detected skin trends, the product recommendation computing device 110 provides a recommendation for one or more skincare products to address the skin trends. The product recommendation computing device 110 may also receive feedback about the recommended one or more skincare products, and may use this feedback to improve recommendations for future requests.

Figure 2:
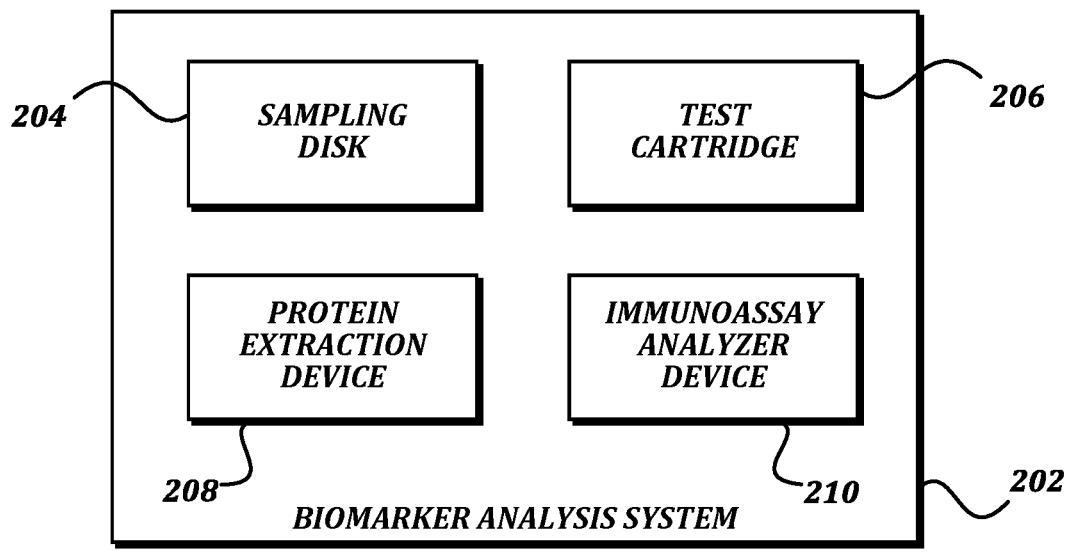
FIG. 2 is a block diagram that illustrates further details of an example embodiment of a biomarker analysis system and an example embodiment of a product recommendation computing device according to various aspects of the present disclosure.
Figure 2:
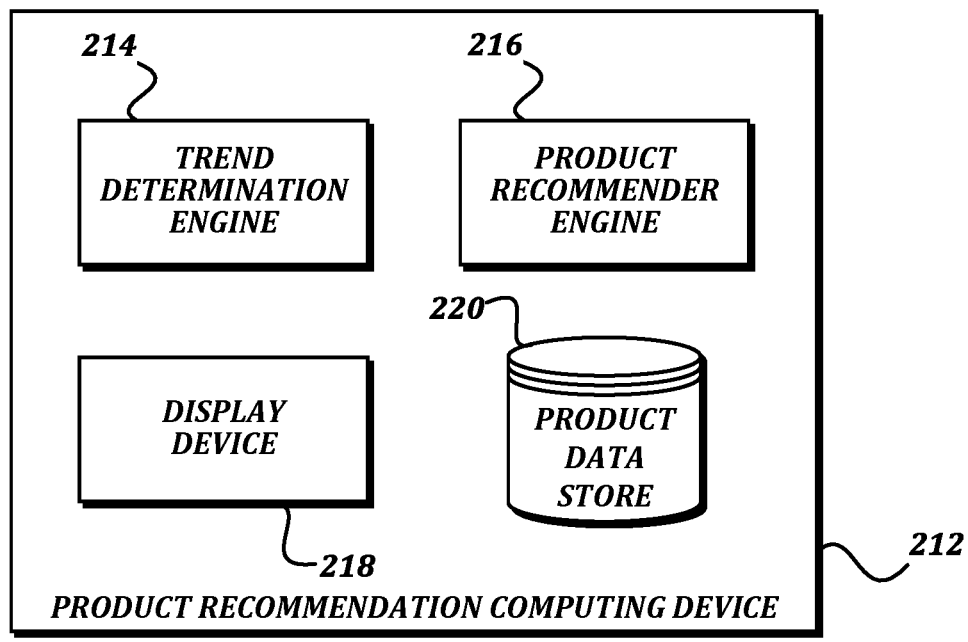

FIG. 2 is a block diagram that illustrates further details of an example embodiment of a biomarker analysis system and an example embodiment of a product recommendation computing device according to various aspects of the present disclosure.

In some embodiments, the biomarker analysis system 202 includes one or more devices that provide a measurement of biomarkers sampled from a subject. In some embodiments, such sampling is done quickly and non-invasively, thus allowing the biomarker sampling to take place in an outpatient clinical or retail environment. In the illustrated embodiment, the biomarker analysis system 202 includes a sampling disk 204, a test cartridge 206, a protein extraction device 208, and an immunoassay analyzer device 210.

In some embodiments, the sampling disk 204 comprises a substrate and an adhesive. The adhesive is suitable for removably attaching the sampling disk 204 to the skin of a subject and obtaining a sample of skin cells therefrom. Though a sampling disk 204 is described, in some embodiments, an adhesive device of another shape, including but not limited to a rectangle or a tape may be used. In some embodiments, a swab, a wipe, or another device usable to collect a skin cell sample may be used instead of an adhesive device. One non-limiting example of a device that is suitable for use as a sampling disk 204 is a D-SQUAME® sampling disk produced by CuDerm Corporation, though other devices could be used.

In some embodiments, the protein extraction device 208 is configured to remove samples from sampling disks 204 and convert them into a form that can be provided to a test cartridge 206 for processing. In some embodiments, the protein extraction device 208 may include a container in which the sampling disk 204 may be placed along with a buffer solution. The protein extraction device 208 may also include a device for agitating, centrifuging, or otherwise processing the container such that the proteins from the collected skin sample are released from the sampling disk 204 and dissolved in the buffer solution.

In some embodiments, the test cartridge 206 is approximately the size of a credit card, and includes an inlet in which a droplet (approximately 300) of the solution containing the proteins from the collected skin sample may be placed. The inlet may be coupled to one or more microfluidic channels through which the solution will automatically flow. In some embodiments, antibodies may be deposited within the one or more microfluidic channels, and antigens within the sample may react with the antibodies. This reaction may cause fluorescent beads associated with the antibodies to fluoresce according to the concentrations of the proteins being measured. The immunoassay analyzer device 210 may accept the test cartridge 206, and may measure the concentrations of the proteins of interest within the sample. In some embodiments, the immunoassay analyzer device 210 may do so by using laser light to determine which fluorescent beads are fluorescing. Once measured, the immunoassay analyzer device 210 may provide the determined protein concentrations to other components of the system using any suitable technique, including but not limited to presenting the protein concentrations on a display, printing the protein concentrations on a paper receipt, and electronically transmitting the determined protein concentrations to another device. One non-limiting example of an immunoassay analyzer device 210 (and its associated test cartridges 206) are the FREND™ System provided by NanoEnTek Inc.

In some embodiments, the product recommendation computing device 212 is a computing device configured to receive protein concentration information from the biomarker analysis system 202, determine one or more skin trends based on the protein concentration information, and determine product recommendations based on the protein concentration information. In some embodiments, the product recommendation computing device 212 is also configured to receive feedback on recommended products, which the product recommendation computing device 212 can then use to improve future product recommendations.

In some embodiments, the product recommendation computing device 212 may be a mobile computing device such as a smartphone or a tablet computing device. In some embodiments, the product recommendation computing device 212 may be a desktop computing device or a laptop computing device. In some embodiments, the product recommendation computing device 212 may include more than one computing device, such as a user computing device configured to provide a user interface and one or more server computing devices configured to provide computational functionality (such as the functionality of the trend determination engine 214 and/or the product recommender engine 216 described below). In such embodiments, the user computing device and the one or more server computing devices may communicate via any suitable communication technology or technologies, such as a wired technology (including but not limited to Ethernet, USB, or the Internet) or a wireless technology (including but not limited to WiFi, WiMAX, 3G, 4G, LTE, or Bluetooth).

In the illustrated embodiment, the product recommendation computing device 212 includes a trend determination engine 214, a product recommender engine 216, a display device 218, and a product data store 220.

In some embodiments, the trend determination engine 214 is configured to receive protein biomarker concentration information from the biomarker analysis system, and to determine skin trends using the correlation information that has been clinically determined.

In some embodiments, the product recommender engine 216 is configured to receive the skin trend information and to determine one or more products based on the skin trend information. In some embodiments, the product recommender engine 216 may directly use the protein biomarker concentration information to determine the one or more products. In some embodiments, the product recommender engine 216 may also collect additional information to inform the selection of the one or more products, including but not limited to presenting a questionnaire that provides environmental information relevant to the user 90. In some embodiments, the product recommender engine 216 may also collect feedback from the user 90 regarding the selected one or more products, and may use that feedback to improve recommendations for future products for the user 90 and for other users.

In some embodiments, the display device 218 may be an LED display, OLED, display, or other type of display that presents a user interface to the user 90. The user interface may include presentations of the recommended products, and may include a form or other type of interface that allows the user 90 to provide feedback for the recommended products.

In some embodiments, the product data store 220 may be used to store relevant information for each user 90, including but not limited to the protein biomarker concentration information, the skin trends determined by the trend determination engine 214, the one or more products recommended by the product recommender engine 216, and the feedback collected by the product recommender engine 216.

Figure 3:
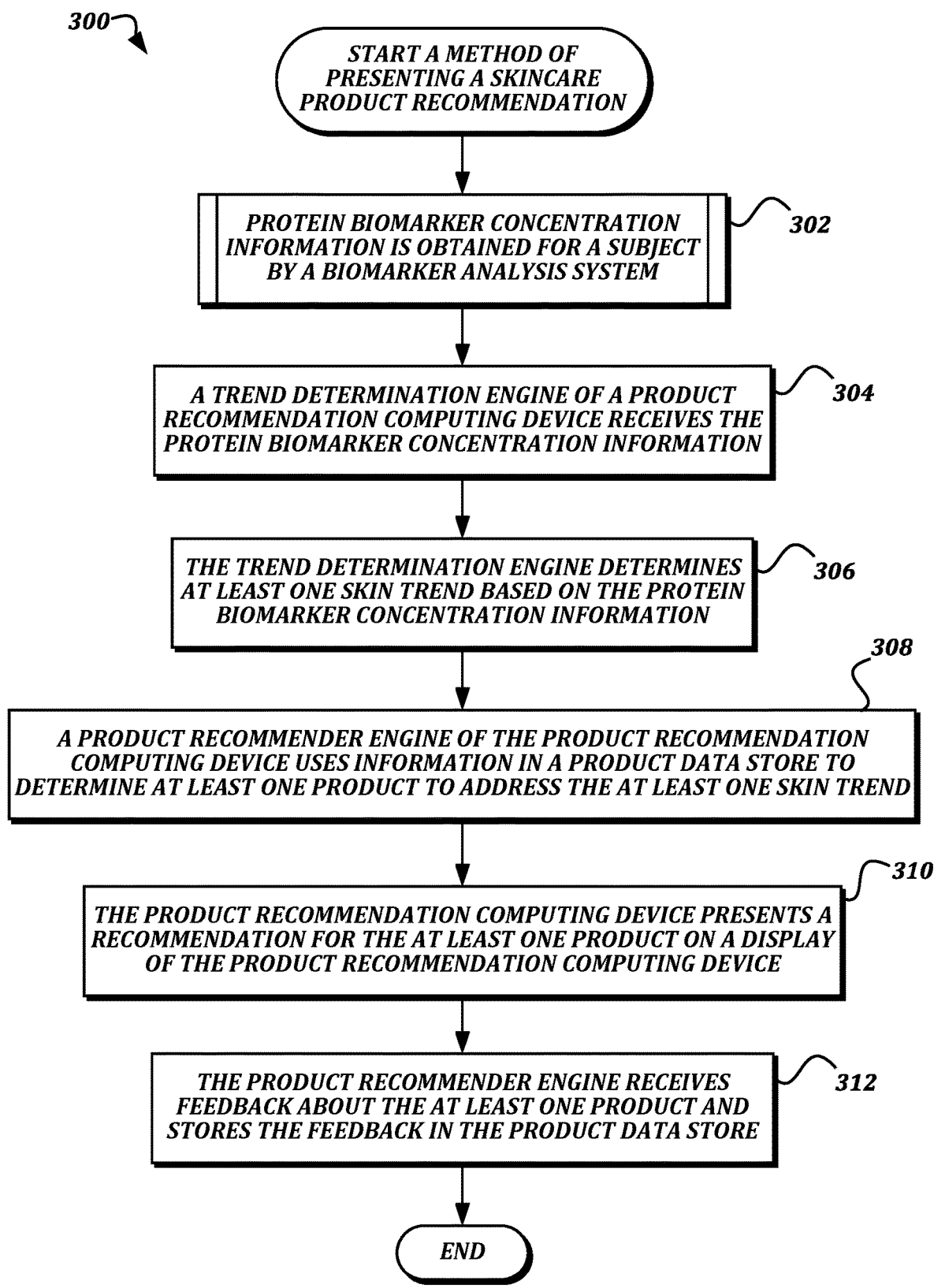
FIG. 3 is a flowchart that illustrates an example embodiment of a method of presenting a skincare product recommendation according to various aspects of the present disclosure.

FIG. 3 is a flowchart that illustrates an example embodiment of a method of presenting a skincare product recommendation according to various aspects of the present disclosure. From a start block, the method 300 advances to procedure block 302, where a procedure is executed wherein protein biomarker concentration information is obtained for a subject by a biomarker analysis system 202. Any suitable procedure may be used to collect the protein biomarker concentration information, including but not limited to the procedure 400 illustrated in FIG. 4 and described below.

At block 304, a trend determination engine 214 of a product recommendation computing device 212 receives the protein biomarker concentration information. In some embodiments, the protein biomarker concentration information is received from the biomarker analysis system 202 by the trend determination engine 214 via a network. The network may be a wireless network, including but not limited to a Wi-Fi network, a cellular network (including but not limited to a 3G network, a 4G network, a 5G network, or an LTE network), or a Bluetooth network; a wired network, including but not limited to an Ethernet network, a USB network, or a FireWire network; and/or any other type of network. In some embodiments, the protein biomarker concentration information may be displayed by a display device (not illustrated) of the biomarker analysis system 202, and the protein biomarker concentration information may be manually entered into an interface presented by the display device 218, or may be captured from the display device of the biomarker analysis system 202 by a camera of the product recommendation computing device 212.

At block 306, the trend determination engine 214 determines at least one skin trend based on the protein biomarker concentration information. Preliminary clinical studies have suggested linkage between five biomarkers (FLG2, TG3, IDE, LCN1, and YKL40) and clinical signs of aging. Example predictive performances (ROC curves) of these biomarkers for various clinical signs of aging are as follows:

| Clinical Sign | Biomarker | p value | Accuracy | Sensitivity | Specificity | kappa | Cutt off (ng/ml) |
|---|---|---|---|---|---|---|---|
| Shiny skin | FLG2 | 0.0000 | 66% | 77% | 53% | 0.30 | <166.3 |
| Rough skin | FLG2 | 0.0001 | 63% | 72% | 53% | 0.25 | <144.1 |
| Uneven skin tone | TG3 | 0.2048 | 60% | 67% | 46% | 0.12 | <26.8 |
| Eye wrinkles | IDE | 0.0000 | 62% | 67% | 58% | 0.24 | <11.5 |
| Photoaging | TG3 | 0.0243 | 57% | 66% | 48% | 0.14 | <24.9 |
| Loss of Elasticity | LCN1 | 0.0201 | 57% | 57% | 56% | 0.13 | >44.3 |
| Dilated pores | YKL40 | 0.2245 | 54% | 61% | 51% | 0.10 | >2.4 |

Preliminary studies have also suggested a link between biomarkers and whether a subject is a responder or a non-responder to retinol and proxylane. Preliminary clinical studies have suggested that the YKL40 and TG3 biomarkers indicate that a subject will be responsive to retinol for improvement of underneath eye wrinkles, that the TG3 and LCN1 biomarkers indicate that a subject will be responsive to retinol for improvement of full-face dyschromia, and that the YKL40 biomarker indicates that a subject will be responsive to proxylane for improvement of erythrosis. In some embodiments, the trend determination engine 214 uses one or more of these clinically suggested relationships and the biomarker concentration information to predict one or more facial aging trends based on the biomarker concentration information. In some embodiments, the trend determination engine 214 may store the biomarker concentration information and/or the predicted facial aging trends/skin trends in the product data store 220.

At block 308, a product recommender engine 216 of the product recommendation computing device 212 uses information in a product data store 220 to determine at least one product to address the at least one skin trend. In some embodiments, the product data store 220 stores records identifying a plurality of products, and each record may associate a given product with one or more skin trends addressed by the given product. Each record may also include one or more ingredients present in the given product. The product data store 220 may also store records regarding what users have received recommendations of what products, and may store records regarding feedback received from the users regarding the recommended products. In some embodiments, the product data store 220 may also store information about the users themselves, including but not limited to age, gender, demographic information, and location, that can be used to group users with other similar users based on the stored information. In some embodiments, the product recommender engine 216 uses the records of previous recommendations, the feedback received, and the information about the users as input into a collaborative filter, a content-based filter, or a hybrid filter in order to generate recommendations for the user 90 to address the detected at least one skin trend.

At block 310, the product recommendation computing device 212 presents a recommendation for the at least one product on a display device 218 of the product recommendation computing device 212. In some embodiments, the recommendation may be presented as a link to a webpage or an app from which the user 90 can purchase the recommended at least one product. In some embodiments, the recommendation may be presented as instructions for how to obtain the product from a retailer.

At block 312, the product recommender engine 216 receives feedback about the at least one product and stores the feedback in the product data store 220. In some embodiments, the product recommender engine 216 may use the display device 218 to present a feedback form to the user 90 through which the feedback is collected, and the feedback form may be presented at some future time after the user 90 has had a chance to use the at least one product. In some embodiments, the product recommender engine 216 may collect implicit feedback by monitoring purchases made by the user 90, and ascribing positive feedback values to additional purchases of the at least one recommended product. In some embodiments, the product recommender engine 216 may collect feedback by reviewing social media postings by the user 90 that mention the at least one product, and conducting a sentiment analysis on the postings. In some embodiments, the product recommender engine 216 may collect feedback by receiving results of a future analysis by the biomarker analysis system 202 and the trend determination engine 214, and may determine feedback based on whether the detected skin trend has been addressed. In some embodiments, the feedback stored in the product data store 220 is used by the collaborative filter, the content-based filter, or the hybrid filter of the product recommender engine 216 to improve future recommendations.

The method 300 then proceeds to an end block and terminates.

Figure 4:
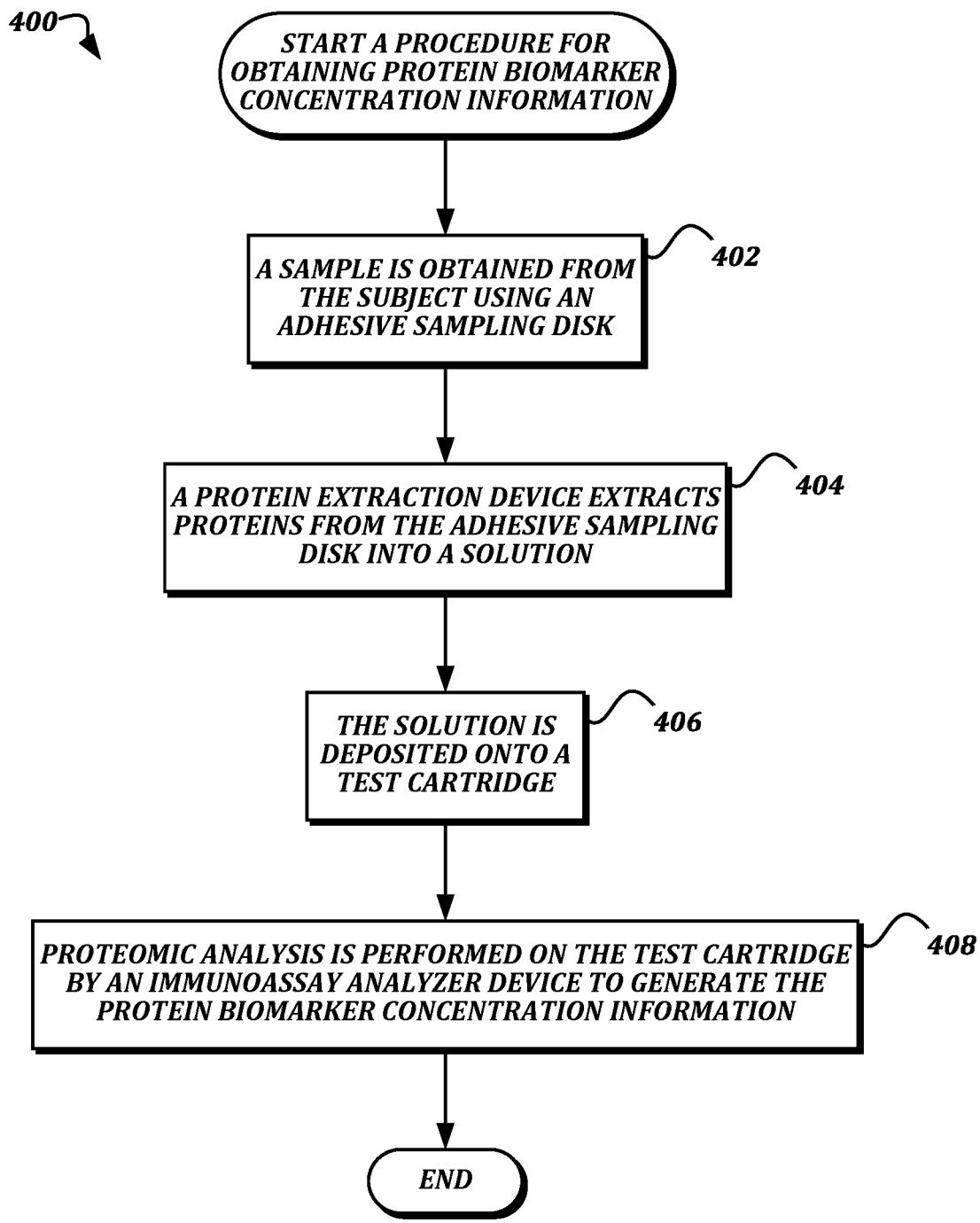
FIG. 4 is a flowchart that illustrates an example embodiment of a procedure for obtaining protein biomarker concentration information according to various aspects of the present disclosure.

FIG. 4 is a flowchart that illustrates an example embodiment of a procedure for obtaining protein biomarker concentration information according to various aspects of the present disclosure. The procedure 402 is a non-limiting example of a procedure suitable for use at block 302 of FIG. 3 for obtaining protein biomarker concentration information for a subject.

From a start block, the procedure 4D00 advances to block 402, where a sample is obtained from the subject using a sampling disk 204. In some embodiments, the sampling disk 204 may be attached to the skin of the subject via an adhesive. In some embodiments, the sampling disk 204 may absorb substances such as sweat, sebum, and other skin secretions. In some embodiments, the adhesive of the sampling disk 204 may collect skin cells from the skin of the subject. In some embodiments, the sampling disk 204 may be placed on the skin and removed from the skin multiple times to collect the skin sample. In some embodiments, a weight or pressure may be applied on top of the sampling disk 204, and/or the sampling disk 204 may be left in place for a specific amount of time, in order to obtain a consistent sample.

Next, at block 404, a protein extraction device 210 extracts proteins from the sampling disk into a solution. In some embodiments, the protein extraction device 210 may apply the solution to the sampling disk in order to dissolve the skin cells, skin secretions, or other sampled matter into the solution. In some embodiments, the sampling disk 204 may be placed in a buffer solution, and may then be shaken to cause the skin sample to be dissolved in the solution.

At block 406, the solution is deposited onto a test cartridge 206. In some embodiments, a droplet of the solution created by the protein extraction device 210 that includes the proteins from the sampling disk is placed in an inlet of the test cartridge 206. At block 408, proteomic analysis is performed on the test cartridge 206 by an immunoassay analyzer device 208 to generate the protein biomarker concentration information. In some embodiments, the test cartridge 206 is inserted into the immunoassay analyzer device 208, which uses laser light to measure the fluorescing beads and thereby determine the concentrations of the protein biomarkers in the skin sample. The procedure 400 then advances to an end block and terminates. The protein biomarker concentration information may be displayed on a screen of the immunoassay analyzer device 208, may be transmitted electronically to another device, or may be provided to another device in some other way in order to allow the protein biomarker concentration information to be used for recommending and updating skincare product formulations (or for any other purpose).

While illustrative embodiments have been illustrated and described, it will be appreciated that various changes can be made therein without departing from the spirit and scope of the invention.

The invention claimed is:

1. A computer-implemented method of providing a skincare product recommendation for a subject, the method comprising:
    receiving, by a computing device, protein biomarker concentration information from an immunoassay analyzer device configured to determine protein concentrations by measuring fluorescence;
    determining, by the computing device, at least one skin trend based on the protein biomarker concentration information;
    determining, by the computing device, at least one skincare product associated with the at least one skin trend; and
    presenting, by the computing device, a recommendation of the at least one skincare product via a display.

2. The method of claim 1, wherein determining the at least one skincare product includes providing the at least one skin trend and information associated with the subject to a recommender engine that uses at least one of a collaborative filter, a content-based filter, and a hybrid filter to generate recommendations.

3. The method of claim 2, further comprising:
    receiving feedback about the at least one skincare product; and
    updating the recommender engine using the feedback.

4. The method of claim 1, further comprising receiving one or more questionnaire responses;
    wherein the determination of at least one skin trend is further based on the one or more questionnaire responses.

5. The method of claim 1, wherein the protein biomarker concentration information includes information about a concentration of at least one of an FLG2 biomarker, a TG3 biomarker, an IDE biomarker, an LCN1 biomarker, and a YKL40 biomarker.

6. The method of claim 1, wherein the at least one skin trend includes development of at least one of shiny skin, rough skin, uneven skin tone, eye wrinkles, photo-aging, loss of elasticity, and dilated pores.

7. A system for providing a skincare product recommendation for a subject, the system comprising:
    circuitry for receiving protein biomarker concentration information from an immunoassay analyzer device configured to determine protein concentrations by measuring fluorescence;
    circuitry for determining at least one skin trend based on the protein biomarker concentration information;
    circuitry for determining at least one skincare product associated with the at least one skin trend; and
    circuitry for presenting a recommendation of the at least one skincare product via a display.

8. The system of claim 7, wherein determining the at least one skincare product includes providing the at least one skin trend and information associated with the subject to a recommender engine that uses at least one of a collaborative filter, a content-based filter, and a hybrid filter to generate recommendations, and wherein the system further comprises:
    circuitry for receiving feedback about the at least one skincare product; and
    circuitry for updating the recommender engine using the feedback.

9. The system of claim 7, further comprising circuitry for receiving one or more questionnaire responses;
    wherein the determination of at least one skin trend is further based on the one or more questionnaire responses.

10. The system of claim 7, wherein the protein biomarker concentration information includes information about a concentration of at least one of an FLG2 biomarker, a TG3 biomarker, an IDE biomarker, an LCN1 biomarker, and a YKL40 biomarker.

11. The system of claim 7, wherein the at least one skin trend includes development of at least one of shiny skin, rough skin, uneven skin tone, eye wrinkles, photo-aging, loss of elasticity, and dilated pores.

12. The system of claim 7, wherein the circuitry is included in a smartphone or a tablet computing device.

13. A computing device configured to provide a skincare product recommendation for a subject, by:
    receiving, by the computing device, protein biomarker concentration information from an immunoassay analyzer device configured to determine protein concentrations by measuring fluorescence;
    determining, by the computing device, at least one skin trend based on the protein biomarker concentration information;
    determining, by the computing device, at least one skincare product associated with the at least one skin trend; and
    presenting, by the computing device, a recommendation of the at least one skincare product via a display.

14. The computing device of claim 13, wherein determining the at least one skincare product includes providing the at least one skin trend and information associated with the subject to a recommender engine that uses at least one of a collaborative filter, a content-based filter, and a hybrid filter to generate recommendations, and wherein the computing device is further configured to:

receive feedback about the at least one skincare product; and update the recommender engine using the feedback.

15. The computing device of claim 13, wherein the computing device is further configured to receive one or more questionnaire responses;
   wherein the determination of at least one skin trend is further based on the one or more questionnaire responses.

16. The computing device of claim 13, wherein the protein biomarker concentration information includes information about a concentration of at least one of an FLG2 biomarker, a TG3 biomarker, an IDE biomarker, an LCN1 biomarker, and a YKL40 biomarker.

17. The computing device of claim 13, wherein the at least one skin trend includes development of at least one of shiny skin, rough skin, uneven skin tone, eye wrinkles, photoaging, loss of elasticity, and dilated pores.

18. The computing device of claim 13, wherein the computing device is a smartphone or a tablet computing device.

\* \* \* \* \*